United States Patent
Yvin et al.

(10) Patent No.: US 6,855,325 B1
(45) Date of Patent: Feb. 15, 2005

(54) USE OF HYPO-OSMOTIC SALINE SOLUTIONS AND MEDICINE BASED ON SAID SOLUTIONS

(75) Inventors: Jean-Claude Yvin, Saint-Malo (FR); Bénédicte Halley, Caen (FR)

(73) Assignee: Laboratoires GOEMAR S.A., Saint-Malo Cedex (FR)

( * ) Notice: Subject to any disclaimer, the term of this patent is extended or adjusted under 35 U.S.C. 154(b) by 24 days.

(21) Appl. No.: 10/048,249

(22) PCT Filed: Jul. 25, 2000

(86) PCT No.: PCT/FR00/02135

§ 371 (c)(1),
(2), (4) Date: May 2, 2002

(87) PCT Pub. No.: WO01/07073

PCT Pub. Date: Feb. 1, 2001

(30) Foreign Application Priority Data

Jul. 27, 1999 (FR) .................................... 99 09743

(51) Int. Cl.$^7$ .................... A61K 7/00; A61K 33/00; A61K 33/14
(52) U.S. Cl. .................. 424/401; 424/400; 424/600; 424/677; 424/680
(58) Field of Search ................. 424/400, 401, 424/600, 677, 680; 514/908, 910, 912, 914, 915

(56) References Cited

FOREIGN PATENT DOCUMENTS

| CN | 1 129 099 | 8/1996 |
|----|-----------|--------|
| DE | 43 39 750 | 5/1995 |
| FR | 2 778 562 | 11/1999 |
| WO | WO 00 01395 | 1/2000 |

OTHER PUBLICATIONS

Database WPI Section Ch, Week 199324, Derwent Publications Ltd., Lond, GB, AN 1993–191439, XP002138626, and JP 05 1171585 A (Sasaki Kagaky Yakyhin KK), May 14, 1993 *Abstract*.

*Primary Examiner*—Shelley A. Dodson
(74) *Attorney, Agent, or Firm*—McDonnell Boehnen Hulbert & Berghoff LLP

(57) ABSTRACT

Treatment for preventing and limiting the release of the chemical mediators which are responsible of the starting of cutaneous inflammatory phenomena comprising administration to a patient of hypoosmotic saline solutions.

9 Claims, No Drawings

USE OF HYPO-OSMOTIC SALINE SOLUTIONS AND MEDICINE BASED ON SAID SOLUTIONS

The present application is a National Phase of PCT/FR00/02135, filed Jul. 25, 2000, which claims priority to French Patent Application No. FR 99/09743, filed Jul. 27, 1999.

The invention relates to a new use of hypoosmotic saline solutions in view of the obtention of a medicine.

It also relates to a medicine on the basis of these hypoosmotic saline solutions, this medicine being intended to prevent and to limit the release of the chemical mediators which are responsible of the starting of the inflammatory phenomena of the skin.

The chemical mediators in question are freed or released in the case of certain diseases of the skin as well as under the action of the constituents of certain cosmetic products especially of certain products intended for the treatment of the skin.

In that respect, in the case of diseases of the group comprising allergic reactions, i.e. eczema (delayed hypersensitivity) and urticaria (immediate hypersensitivity), psoriasis, irritating poll evils in general, atopical dermatitis, bums and prurigo, one observes the production, on the level of especially the epidermis, of a more or less important release of chemical mediators among which interleukin IL-8, on which is based the starting of the inflammatory phenomena of the skin which phenomena may be come very awkward to the patient.

These phenomena can also occur in the case of sun erythema or sun burn and in the case of insect bits or of vegetal stings.

The same phenomena occurs in the case of certain patients which are in good health but whose skin is sensitive, irritated or reactive when put into contact with certain cosmetic products whose constituents, which are not always identified as such, play the role of pro-inflammatory agent on the level of the skin, and when playing that role, cause the release of the chemical mediators which in turn cause the starting of the inflammatory phenomena which most frequently express themselves by redness especially on the level of the face or forehead.

It is already known to combat these pathologies by having recourse to medicines based on corticosteroids such as dexamethasone or on anti-inflammatory, non steroidic substances, such as bufexamac.

The results obtained with corticosteroids and with non steroidic anti-inflammatory substances are satisfactory but it is well known that these products have side effect which are sometimes troublesome.

The object of the invention is above all to cope with the drawbacks of the prior art and to provide for the treatment of the inflammatory phenomena in question a medicine free of side effects.

And the applicants have had the merit of having found after thorough researches that this object is reached when using a medicine, obtained by the use of hypoosmotics saline solutions and intended to a treatment adapted to prevent and to limit the release—as well in the case of the diseases of the above defined group as under the actions of the constituents of certain, cosmetic products, these constituents playing the role of pro-inflammatory agents—of the chemical mediators which are responsible of the starting of cutaneous inflammatory phenomena The hypoosmotic saline solution in question presents:

a pH of from 5,0 to 8,30, a resistivity of from 52 to 370 Ω and preferably from 57 to 85 Ω, a density of from 1,002 to 1,008, a dry matter content of from 0,2 to 0,9%, an osmolarity comprise between 100 mOs and 305 mOs/kg (milliosmols/kg), preferably between 140 and 240 mOs/kg, and a chemical constitution whose principal constituents appear from Table 1 hereafter:

TABLE I

| | |
|---|---|
| Sodium (Na) | from 600 to 2000 mg/l |
| Potassium (K) | from 6 to 40 mg/l |
| Chlorures (Cl) | from 2000 to 5800 mg/l |
| Calcium (Ca) | from 200 to 300 mg/l |
| Magnesium (Mg) | from 1000 to 1200 mg/l |
| Sulfate ($SO_4$) | from 2000 to 3000 mg/l |

By way of consequence, the invention consists in the use of hypoosmotic saline solutions, especially prepared starting from sea water, for the obtention of a medicine intended for a treatment preventing and limiting the release of the chemical mediators which are responsible of the starting of the cutaneous inflammatory phenomena.

For the preparation of the hypoosmotic solutions, used according to the invention, it is possible to proceed as hereafter indicated.

Recourse is made as far as the raw material is concerned, to a sea water picked up preferably at a depth of 5 to 10 meters in a zone in which the stream or the current of the water is strong and which is characterised by a content in salts higher than 32 g/l.

The said water is analysed, decanted and then rapidly:

subjected to electrodyalisis in order to remove sodium chloride and to bring its osmolarity to a value comprised between 100 and 305 mOs/kg, filtrated, stored under sterile conditions, especially in a stainless steel vessel.

It is then again analysed in order to check:

its sterility its osmolarity.

Finally it can be conditioned under sterile conditions in an especially treated room under controlled atmosphere.

The researches on which is based the invention comprise experiences which show that the hypoosmotic saline solutions used according to the invention as well as the well known isoosmotic saline solutions and as well as certain corticosteriods such as dexamethasone, are not cytotoxic with respect to keratinocytes, while their ability to prevent and to limit the release under the influence of certain diseases or certain pro-inflammatory agents of the chemical mediators which are responsible of the starting of the cutaneous inflammatory phenomena is higher than that obtained when using the two comparative products which are hereabove identified.

For the examination of the toxicity, normal human epidermic keratinocytes were used which were taken from epidermis samples; they consist especially in keratinocytes isolated from the remains of an operation of an abdominal plasty carried out on a 27 years old woman (patient No. 10020).

These keratinocytes were cultivated at 37° C. in a culture medium intended for keratinocytes or MCK, i.e. the one which is marketed under the designation "SFM defined-keratinocyte medium" by the company GIBCO under a humid atmosphere containing 5% of $CO_2$ until confluence of the monolayers.

The tested products were consisting of three hypoosmotic saline solutions designated by J, I and H whose resistivities are respectively 57,30 Ω, 64,93 Ω and 74,34 Ω and whose principal constituent elements appear in the following table II:

TABLE II

| Constituents | Units | H | I | J |
| --- | --- | --- | --- | --- |
| Sodium (Na) | mg/l | 765 | 1130 | 1370 |
| Potassium (K) | mg/l | 11,2 | 20,8 | 27,4 |
| Chlorides (Cl) | mg/l | 2930 | 3797 | 4248 |
| Calcium (Ca) | mg/l | 290 | 310 | 330 |
| Magnesium(Mg) | mg/l | 1130 | 1200 | 1200 |
| Sulfates ($SO_4$) | mg/l | 2570 | 2570 | 2600 | the isoosmotic solution marketed by the applicants under the trademark "PHYSIOMER" designated by K, the dexamethasone and the physiological serum marketed under the trademark BABISOL.

These six products were incubated during 4 hours in the cultures of the keratinocytes.

Before the incubation, the cells, i.e. the keratinocytes, were rinsed with the tested products in order to eliminate any trace of culture medium.

The saline solutions J, I, H, and K and the physiological serum were used without dilution.

The dexamethasone has been tested at 10 μM in the medium MCK.

The cultures of keratinocytes were incubated in the presence of the six products during 4 hours at 37° C., under a humid atmosphere containing 5% of $CO_2$.

The control cultures, incubated in the medium MCK in the absence of the six products, were carried out in parallel.

All these trials were carried out three times.

The cytotoxic effect of the six tested products has been estimated by determining the percentage of proteins remaining in the keratinocytes after 4 hours of incubation in the presence of the different products, being understood that when the keratinocytes are incubated in the MCK culture medium, the loss in proteins is equal to zero, the keratinocytes keeping consequently 100% of their proteins.

The percentages of proteins remaining in the presence of the six tested products are collected in the following table III.

TABLE III

| Control MCK | Dexamethasone 10 μM in MCK | Physiological serum | J | I | H | K |
| --- | --- | --- | --- | --- | --- | --- |
| 100 | 89 | 32 | 86 | 73 | 86 | 86 |

The results are expressed in mg of proteins/ml.

From the examination of the values collected in Table III, it appears:

that the physiological serum is highly cytotoxic, that dexamethasone and the products J, H and K are equivalent and very few cytotoxic, the hypoosmotic saline solution I being a little less satisfactory from this point of view.

Then the ability of the hypoosmotic saline solutions used according to the invention to prevent and to limit the release under the influence of certain diseases or certain pro-inflammatory agents of the chemical mediators responsible for the starting of the cutaneous inflammatory phenomena has been examined.

The tested chemical mediator was interleukine IL-8.

The pro-inflammatory agent was consisting of the MCK culture medium which appears to be at the origin of a strong release of interleukine IL-8 in cultures of keratinocytes.

The procedure was similar to that used in the above disclosed tests concerning the estimation of the cytotoxicity of the various tested products.

These products were the same.

The duration of the incubation was also equal to 4 hours.

Under the influence of the MCK medium, the release of interleukine IL-8 was 100 pg/mg of proteins; in that same medium determination has been carried out of the amounts of interleukine IL-8 released in the presence of the six tested products, i.e. on the one hand, the products J, I, H, K as well as physiological serum which were used without dilution and, on the other hand, dexamethasone which has been used at the rate of 10 μM in the MCK medium.

The thus found values are collected in the following Table IV.

TABLE IV

| Control MCK | Dexamethasone 10 μM in MCK | Physiological serum | J | I | H | K |
| --- | --- | --- | --- | --- | --- | --- |
| 100 | 74 | 165 | 40 | 42 | 50 | 89 |

The results are expressed in pg of IL-8/mg of proteins.

From the examination of the values recorded in Table IV, it appears:

that the effect of the physiological serum is to increase the release of IL-8, that the isoosmotic saline solution K limits a little the release of IL-8 and that dexamethasone limits it a little bit more but, above all, that the hypoosmotic saline solutions J, I and H limit the said release very strongly.

From a practical point of view, the medicines obtained by the use of the hypoosmotic saline solutions in view of a treatment for preventing and limiting the release of the chemical mediators which are responsible from the starting of the cutaneous inflammatory phenomena may be presented under the following forms:

emulsions (creams, milks, multiple emulsions, micro-emulsions, nano-emulsions and others), gels (aqueous or oily), pastes (toothpastes, masks and others), solutions (aqueous or oily), i.e. lotions and others, suspensions and transdermal devices.

In order to illustrate the foregoing, hereafter are provided two examples of such medicines, i.e. an anti-itching cream and a tooth paste which is efficient against gingival inflammation.

1. Anti-Itching cream

| | |
| --- | --- |
| Demineralised water | 44,8% |
| Glycerin | 5% |
| Solution (I) of sea water containing 7 g/l | 20% |
| Laureth-9 | 1,5% |

-continued

| | |
|---|---|
| PEG-100 Stearat glyceryl stearat | 6% |
| Cetylic alcohol | 2% |
| Isononyl isoanoate | 2% |
| Cetearyl octanoate | 8% |
| Hexyldecyl stearate | 6,5% |
| Cyclomethicon | 2% |
| Preserving agents | 1% |
| Polyacrylamid isoparaffin laureth-7 | 1,2% |
| 2. Toothpaste efficient against gingival inflammation | |
| Solution (I) of sea water containing 7 g/l | 45,9% |
| Calcium carbonate | 30,9% |
| Sorbitol | 8% |
| Sodium monofluorophosphate | 0,8% |
| Carraghenan | 2% |
| Hydrated silica | 1% |
| Lithothamn | 11% |
| Aroma | 0,3% |
| Preserving agent | 0,1% |

In order to combat the side effects which are sometimes embarrassing and which occur in the case of people which are especially sensitive when using certain cosmetic products, it is possible to incorporate in the said cosmetic products the medicine obtained by the use of hypoosmotic saline solutions in view of the treatment of preventing and limiting the release of chemical mediators which are responsible of the starting of the cutaneous inflammatory phenomena.

An another object of the invention is consequently the use in cosmetic products of the medicine obtained by the use of hypoosmotic saline solutions in view of the treatment for preventing and limiting the release of chemical mediators which are responsible of the starting of cutaneous inflammatory phenomena.

It is true that in the case of cosmetic products the inflammatory phenomena above mentioned generally are limited to several cutaneous rednesses.

But even these manifestations, which are mostly mild or benign, affect the persons concerned.

In order to prevent the said manifestations, the medicine in question is incorporated in cosmetic products in connection with which the phenomena in question have been noticed.

In order to illustrate the fore-going, two examples are given of cosmetic products comprising the said medicines, i.e. a calming lotion and a milk to take off the make-up, both intended for sensitive skins.

| | |
|---|---|
| 3. Calming lotion for sensitive skins | |
| Hypotonic (J) solution of sea water containing 8 g/l | 91,3% |
| Pyrrolidon sodium carbosylate | 3,0% |
| Extract of algae | 2,0% |
| Polysorbate 20 | 2,0% |
| Glycerin | 1,0% |
| Preserving agent | 0,7% |
| 4. Milk to take off the make up intended for sensitive skins | |
| Purified water | 60,9% |
| Solution (H) of hypotonic sea water containing 6 g/l | 18,6% |
| Extract of algae | 6% |
| Propylene glycol | 3% |
| Cetylic alcohol | 2,5% |
| Sorbitol | 2% |
| Glyceryl stearate | 1,5% |
| Fatty acid ethers | 3,45% |
| Stearylic alcohol | 1,05% |

-continued

| | |
|---|---|
| Preserving agent | 1% |
| Sodium hydroxide | qsp pH = 6. |

What is claimed is:

1. A method for preventing and limiting release of chemical mediators responsible for initiating cutaneous inflammatory phenomena comprising administration of a hypoosmotic saline solution to a patient.

2. The method of claim 1, wherein the hypoosmotic saline solution is prepared from sea-water.

3. The method of claim 1, wherein the hypoosmotic saline solution has:

a pH of from 5.0 to 8.30;

a resistivity of from 52 to 370 $\Omega$;

a density of from 1.002 to 1.008;

a dry matter content of from 0.2 to 0.9%;

an osmolarity of between 100 mOs/kg and 305 mOs/kg; and, chemical constituents comprising sodium in an amount from 600 to 2000 mg/l, potassium in an amount from 6 to 40 mg/l, chloride in an amount from 2000 to 5800 mg/l, calcium in an amount from 200 to 300 mg/l, magnesium in an amount from 1000 to 1200 mg/l, and, sulfate in an amount from 2000 to 3000 mg/l.

4. The method of claim 1, wherein the hypoosmotic saline solution has:

a pH of from 5.0 to 8.30;

a resistivity of from 57 to 85 $\Omega$;

a density of from 1.002 to 1.008;

a dry matter content of from 0.2 to 0.9%;

an osmolarity of between 100 mOs/kg and 305 mOs/kg; and, chemical constituents comprising sodium in an amount from 600 to 2000 mg/l, potassium in an amount from 6 to 40 mg/l, chloride in an amount from 2000 to 5800 mg/l, calcium in an amount from 200 to 300 mg/l, magnesium in an amount from 1000 to 1200 mg/l, and, sulfate in an amount from 2000 to 3000 mg/l.

5. The method of claim 1, wherein the hypoosmotic saline solution has:

a pH of from 5.0 to 8.30;

a resistivity of from 52 to 370 $\Omega$;

a density of from 1.002 to 1.008;

a dry matter content of from 0.2 to 0.9%;

an osmolarity of between 140 and 240 mOs/kg; and, chemical constituents comprising sodium in an amount from 600 to 2000 mg/l, potassium in an amount from 6 to 40 mg/l, chloride in an amount from 2000 to 5800 mg/l, calcium in an amount from 200 to 300 mg/l, magnesium in an amount from 1000 to 1200 mg/l, and, sulfate in an amount from 2000 to 3000 mg/l.

6. The method of claim 1, wherein the hypoosmotic saline solution has:

a resistivity of from 57.3 $\Omega$; and, chemical constituents comprising sodium in an amount of 1370 mg/l, potassium in an amount of 27.4 mg/l, chloride in an amount of 4248 mg/l, calcium in an amount of 330 mg/l, magnesium in an amount of 1200 mg/l, and, sulfate, in an amount of 2600 mg/l.

7. The method of claim 1, wherein the hypoosmotic saline solution has:

a resistivity of from 64.93 Ω; and, chemical constituents comprising sodium in an amount of 1130 mg/l, potassium in an amount of 20.8 mg/l, chloride in an amount of 3797 mg/l, calcium in an amount of 310 mg/l, magnesium in an amount of 1200 mg/l, and, sulfate in an amount of 2570 mg/l.

8. The method of claim 1, wherein the hypoosmotic saline solution has:

a resistivity of from 74.34 Ω; and, chemical constituents comprising sodium in an amount of 765 mg/l, potassium in an amount of 11.2 mg/l, chloride in an amount of 2930 mg/l, calcium in an amount of 290 mg/l, magnesium in an amount of 1130 mg/l, and, sulfate in an amount of 2570 mg/l.

9. A cosmetic product comprising a hypoosmotic saline solution.

* * * * *